US006838490B2

(12) United States Patent
Zhang et al.

(10) Patent No.: US 6,838,490 B2
(45) Date of Patent: Jan. 4, 2005

(54) SILICONE RUBBER IN THE FORM OF A FINELY DIVIDED POWDER, METHOD FOR THE PRODUCTION AND THE USE OF THE SAME

(75) Inventors: Xiaohong Zhang, Beijing (CN); Jinliang Qiao, Beijing (CN); Genshuan Wei, Beijing (CN); Jianming Gao, Beijing (CN); Yiqun Liu, Beijing (CN); Shijun Zhang, Beijing (CN); Zhihai Song, Beijing (CN); Jiuqiang Li, Beijing (CN); Yicai Zhu, Beijing (CN)

(73) Assignees: China Petroleum & Chemical Corporation, Beijing (CN); Beijing Research Institute of Chemical Industry China Petroleum & Chemical Corporation, Beijing (CN)

( * ) Notice: Subject to any disclaimer, the term of this patent is extended or adjusted under 35 U.S.C. 154(b) by 0 days.

(21) Appl. No.: 10/049,333

(22) PCT Filed: Jun. 15, 2001

(86) PCT No.: PCT/CN01/00973

§ 371 (c)(1),
(2), (4) Date: Nov. 12, 2002

(87) PCT Pub. No.: WO01/98395

PCT Pub. Date: Dec. 27, 2001

(65) Prior Publication Data

US 2003/0105217 A1 Jun. 5, 2003

(30) Foreign Application Priority Data

Jun. 15, 2000 (CN) .......................................... 00109217 A

(51) Int. Cl.[7] ................................................. C08J 3/075
(52) U.S. Cl. ........................ 522/148; 524/588; 524/267; 524/731
(58) Field of Search .......................... 522/148; 524/267, 524/731, 588

(56) References Cited

U.S. PATENT DOCUMENTS

| 2,763,609 A | 9/1956 | Lewis et al. ................. 204/154 |
| 4,273,634 A | 6/1981 | Saam et al. ............. 204/159.15 |
| 4,362,674 A | 12/1982 | DuPont et al. ................. 264/22 |
| 4,370,160 A * | 1/1983 | Ziemelis ...................... 71/117 |
| 4,594,134 A | 6/1986 | Hanada et al. ................. 522/99 |
| 4,742,142 A | 5/1988 | Shimizu et al. ............... 528/15 |
| 4,743,670 A | 5/1988 | Yoshida et al. ............... 528/15 |
| 4,749,765 A | 6/1988 | Shimizu et al. ............... 528/15 |
| 4,980,167 A * | 12/1990 | Harashima et al. ......... 424/401 |
| 5,082,732 A | 1/1992 | Ueda et al. .................. 428/402 |
| 5,346,932 A * | 9/1994 | Takahashi et al. .......... 523/213 |
| 5,391,594 A * | 2/1995 | Romenesko et al. ........ 523/212 |
| 5,538,793 A | 7/1996 | Inokuchi et al. ............. 428/407 |
| 5,837,793 A | 11/1998 | Harashima et al. ........... 528/29 |
| 6,423,760 B1 * | 7/2002 | Qiao et al. .................. 522/150 |

FOREIGN PATENT DOCUMENTS

| JP | 4202227 | 7/1992 |
| JP | 03095268 | 4/1994 |
| JP | 8109262 | 4/1996 |
| JP | 9169910 | 6/1997 |
| JP | 09249747 | 9/1997 |

OTHER PUBLICATIONS

Paul Hiemenz, "Polymer Chemistry", p. 137, 1984.*
Patent Abstracts of Japan of JP 09249747 Dated Sep. 22, 1997.
Patent Abstracts of Japan of JP 03095268 Dated Apr. 19, 1991.
Min, Y. et al. "Effect of Absorbing Dose on Molecular Weight and Gel Content of Dimethyl Silicone Rubber and Methyl Vinyl Silicone Rubber" China Synthetic Rubber Industry 17 (3) (1994) pp 153–156 Abstract in English.
Xinfang, C. et al. "Enhanced Radiation Crosslinking of Polymers II, Enhanced Radiation Crosslinking of Polydimehtylsiloxanes" Journal of Radiation Research and Radiation Processing, vol. 3, No. 3 (1985) pp 8–12 Abstract in English.
European Polymer Journal, 37(2001)93–98.
CA110:25202v.
Patent Abstracts of Japan of JP 9–169910 Dated June. 30, 1997.
Patent Abstracts of Japan of JP 8–109262 Dated Apr. 30, 1996.
Patent Abstracts of Japan of JP 4–202227 Dated Jul. 23, 1992.

* cited by examiner

Primary Examiner—Margaret G. Moore
(74) Attorney, Agent, or Firm—Ladas & Parry

(57) ABSTRACT

The present invention relates to a novel fully vulcanized powdery silicone rubber, preparation and use thereof. The fully vulcanized powdery silicone rubber is prepared from an latex of organosilicon polymer or copolymer with lower molecular weight via irradiation of high-energy rays. The gel content of the obtained fully vulcanized powdery silicone rubber is at least 60% by weight. The fully vulcanized powdery silicone rubber can be combined with various plastics and is very easy to be dispersed into plastic matrix, and can be used as toughening agent, processing aids or as additives for cosmetics, ink, paint and coatings.

33 Claims, 1 Drawing Sheet

SILICONE RUBBER IN THE FORM OF A FINELY DIVIDED POWDER, METHOD FOR THE PRODUCTION AND THE USE OF THE SAME

The present invention relates to a powdery rubber, more particularly, to a fully vulcanized powdery silicone rubber excluded from vulcanized powdery silicone obtained by chemical crosslinking, a process for preparation and use of the powdery rubber.

It is well known that silicone rubbers can be in the form of blocks, powders, pellets or the like. The vulcanized powdery silicone rubbers have not been disclosed in literatures except the vulcanized powdery silicone rubbers prepared by chemical crosslinking.

A lot of references disclosed the vulcanized powdery silicone rubbers obtained by chemical crosslinking an preparation thereof. For example, U.S. Pat. No. 4,743,670 (issued on May 10, 1998) disclosed a highly dispersed vulcanized powdery silicone rubber and preparation thereof. The vulcanized powdery silicone rubber has a uniform particulate shape and particle size, and a bulk resistance of greater than $10^{13}$ Ω·cm. The process for preparing the vulcanized powdery rubber comprises (1) forming a dispersion of a heat-curable liquid silicone rubber composition in water maintained at a temperature of from 0 to 25° C. and in the absence of surfacants, (2) dispersing the resultant dispersion into a liquid maintained at a temperature of at least 50° C. to obtain said cured silicone rubber in the form of said finely divided powder, and (3) isolating said powder from said liquid.

U.S. Pat. No. 4,742,142 (issued on May 3, 1988) disclosed a process for preparing a powdery silicone rubber that emulsifying a curable liquid silicone rubber composition in a mixture of water and a surfactant at a temperature of from 0 to 25 degrees C., dispersing the curable composition in water heated to a temperature of at least 25 degrees C. and recovering the resultant cured particles.

U.S. Pat. No. 4,749,765 (issued on Jun. 7, 1988) disclosed a process for preparing a powdery silicone rubber having a uniform particle size, which comprises (1) mixing the components at −60 to +5° C. to prepare a liquid silicone rubber composition and keep it at the temperature, (2) spraying the liquid silicone rubber composition obtained in step (1) into hot air at 80 to 200° C. to effect curing of said composition in the sprayed state, (3) recovering the resultant powdery silicone rubber.

U.S. Pat. No. 5,837,793 (issued Nov. 17, 1998) disclosed a vulcanized powdery silicone rubber obtained from vulcanizable silicone composition and preparation thereof. The powdery silicone rubber has a high hydrophilicity an a soft feel, and an average particle size of less than 500 micron. The process for preparing the powdery silicone rubber comprises (1) vulcanizing a vulcanizable silicone composition comprising a specific polyorganosiloxane to form a vulcanized silicone rubber, and (2) drying the vulcanized silicone rubber by spraying. The vulcanization reaction to form the vulcanized silicone rubber can be addition reaction between the alkenyl groups and the silicon-bonded hydrogen, condensation reaction between the silicon-bonded hydroxyl and silicon-bonded hydrogen, reaction induced by an organic peroxide or UV rays.

Generally, the powdery silicone rubbers disclosed in the above-mentioned reference require using a special silicone rubber composition as a feedstock, emulsifying it at a lower temperature and using a chemical crosslinking method to obtain the vulcanized powdery silicone rubber. However, the preparation of said special silicone rubber composition as a feedstock and its latex conventionally used in the art are both complex and expensive, and it is difficult to control the particle size and gel content of the powdery silicone rubber obtained by chemical crosslinking, and therefore a fully vulcanized silicone rubber having a sufficiently small particle size cannot be obtained.

Accordingly, it is highly desired in the art of silicone rubber to provide a fully vulcanized powdery silicone rubber having a particle size in a nanoscale. In addition, it is also desired in the art to provide a method for preparing a fully vulcanized powdery silicone rubber in a facile manner without the need to use the special silicone rubber composition as the feedstock that is expensive and complex in production, as required in the prior art.

After carrying out intensive and extensive research, the inventor has found that a fully vulcanized powdery silicone rubber can be obtained by subjecting the latex of conventional organosilicon polymer or copolymer having lower molecular weight to irradiation of high-energy rays and then drying. The powdery silicone rubber obtained has a controllable particle size that can reach nanoscale and a controllable gel content. Said rubber powder can be used as toughening agent, processing aids etc., as well as the additives for cosmetics, ink, paints and coatings, and has excellent properties, and thus has a promising prospect and great economical significance.

Therefore, one object of the present invention is to provide a novel fully vulcanized powdery silicone rubber.

Another object of the invention is to provide a process for preparing the fully vulcanized powdery silicone rubber.

Yet another object of the present invention is to provide the use of said fully vulcanized powdery silicone rubber for the above-mentioned objects.

The present invention provides a fully vulcanized powdery silicone rubber in nanoscale. Said fully vulcanized powdery silicone rubber particles have an average particle size of less than or equal to $1\mu$, usually from 0.02 to $1\mu$, preferably from 0.05 to $0.5\mu$, more preferably from 0.05 to $0.1\mu$.

In the fully vulcanized powdery silicone rubber according to present invention, each particle is homogeneous, without core-shell or multilayer structure inside. In other words, the individual particle is uniform with respect to the composition, and a heterogeneous phenomenon, such as phase-separation structure, within the particles is not detectable with microscopy available nowadays.

The latex of organosilicon polymer or copolymer having lower molecular weight is selected as the feedstock used in present invention, and the particle size or organosilicon polymer or copolymer particles are fixed by irradiation crosslinking. The irradiation-crosslinked latex is then dried to obtain the fully vulcanized powdery silicone rubber. The average particle size of the fully vulcanized powdery silicone rubber particles is dependent on and remains substantially the same as that of particles in the feed latex. The average particle size of the rubber particles in the feed latex of organosilicon polymer or copolymer having lower molecular weight varies with the processing conditions of polymerization. Generally, the particle size can be less than or equal to $1\mu$, usually from $0.002\mu$ to $1\mu$, preferably from $0.05\mu$ to $0.5\mu$, and more preferably from $0.05\mu$ to $0.1\mu$. Therefore, the average particle size of the fully vulcanized powdery silicone rubber particles obtained in the present invention may be less than or equal to $1\mu$, usually from $0.02\mu$ to $1\mu$, preferably from $0.05\mu$ to $0.5\mu$, and more preferably from $0.05\mu$ to $0.1\mu$.

The latices of organosilicon polymer or copolymer having lower molecular weight used as the feedstock in the present invention include latices of linear or cyclic organosilicon polymer or copolymer having lower molecular weight, preferably linear organosilicon polymer latex having lower molecular weight, such as silicone oil latex, including dimethyl silicone oil latex, diethyl silicone oil latex, methylphenyl silicone oil latex, and methyl hydrosilicone oil latex etc., which are all commercially available. Accordingly, the fully vulcanized powders of such silicone rubbers can be obtained in the present invention.

The present fully vulcanized powdery silicone rubber is a powdery silicone rubber that has a gel content of at least 60% by weight, and is free-flowing without the need of a partitioning agent. If required, the partitioning agent certainly may be introduced into present fully vulcanized powdery silicone rubber so as to further improve the flowability and anti-blocking properties thereof. The present fully vulcanized powdery silicone rubber has a gel content of at least 60% by weight, preferably at least 75% by weight, and more preferably at least 85% by weight. The gel content is a common parameter well known in the art to characterize the crosslinking degree of a rubber, and can be determined by a well-known method in the art.

The present fully vulcanized powdery silicone rubber particle is present in the aggregated form. When the above-mentioned fully vulcanized powdery silicone rubber is mixed with plastics or other materials, these particles are easy to be uniformly dispersed in the matrix and maintain the particle size of the organosilicon polymer or copolymer particles in the feed latex.

The present fully vulcanized powdery silicone rubber can be obtained by vulcanizing the corresponding rubber latex with irradiation. For example, the specific preparing procedure is as follows: irradiating the organosilicon polymer or copolymer latex having lower molecular weight used as the feedstock, in the presence or absence of a crosslinking agent, through irradiation of high-energy rays, to vulcanize it fully. The irradiation of high-energy rays can be selected from the group consisting of cobalt source, X-rays, UV rays and high-energy electron beams, with cobalt source being preferred. The irradiation dose can be 5 to 30 megarads, preferably 10–20 megarads. The fully vulcanized powdery rubber having a particle size that is substantially the same as the size of the organosilicon polymer or copolymer particles in the latex is obtained by drying the irradiated latex. The drying process can be carried out with spray dryer or by precipitation drying method. If the drying is carried out with a spray dryer, the inlet temperature can be controlled at 100 to 200° C., and the outlet temperature at 20 to 80° C.

In the preparation of the present fully vulcanized powdery silicone rubber, there is no restriction on the kinds of the latex of organosilicon polymer or copolymer having lower molecular weight, wherein the specific examples are as described above, with silicone oil latex being preferred. According to the average particle size of the intended fully vulcanized powdery silicone rubber, the latex of rubber particles having corresponding average particle size is selected as a feedstock. Therefore, the average particle size of rubber particles in the latex can be less than or equal to $1\mu$, usually from $0.02\mu$ to $1\mu$, preferably from $0.05\mu$ to $0.5\mu$, and more preferably from $0.05\mu$ to $0.1\mu$. These latices of organosilicon polymer or copolymer having lower molecular weight, such as silicone oil latices, are commercially available.

A crosslinking agent is optionally used in the preparation of the present powdery silicone rubber. The suitable crosslinking agent can be mono-, di-, tri-, tetra-, or multi functional crosslinking agent, and any combination thereof. Examples of said monofunctional crosslinking agent include, but not limited to, isooctyl (meth)acrylate, glycidyl (meth)acrylate; examples of said difunctional crosslinking agent include, but not limited to, 1,4-butandiol di(meth) acrylate, 1,6-hexandiol di(meth)acrylate, neopentyl glycol di(meth)acrylate, divinyl benzene; examples of said trifunctional crosslinking agent include, but not limited to, trimethlolopropane tri(meth)acrylate, pentaerythritol tri(meth) acrylate, examples of said tetrafunctional crosslinking agent include, but not limited to, pentaerythritol tetra(meth) acrylate, ethoxylated pentaerythritol tetra(meth)acrylate; examples of said multifunctional crosslinking agent include, but not limited to, di-pentaerythritol penta(meth)acrylate. In the context of the present application, the term "(meth) acrylate" means acrylate and methacrylate.

The above-mentioned crosslinking agent can be used alone or in any combination thereof, as long as it facilitates the vulcanization under irradiation.

The amount of the crosslinking agent added is generally 0.1 to 10% by weight, preferably 0.5 to 7% by weight, more preferably 0.7 to 5% by weight of the solid content in the latex.

The irradiation of high-energy rays used in the present invention is the conventional cobalt source, X-rays, UV rays or high-energy electron beams, preferably cobalt source. In general, the irradiation dose shall be controlled such that after irradiation and vulcanization of the latex, the gel content therein reaches at least 60% by weight, preferably at least 75% by weight, more preferably at least 85% by weight. The irradiation dose can be in the range of from 5 to 30 megarads, preferably from 10 to 20 megarads.

The average particle size of the present fully vulcanized powdery silicone rubber is determined by the transmission electron microscopy.

The gel content of the present fully vulcanized powdery silicone rubber is determined according to the following procedure: placing the irradiated latex on evaporating dish in dropwise manner, and positioning it in a shady and cool place to form a film; after the weight of the film becomes constant, weighing about 0.1 gram of the film, wrapping it with copper screen, and extracting it in toluene until the weight of the thoroughly dried copper screen and film becomes substantially constant, usually for about 8 hours. Then, the thoroughly extracted copper screen and the latex film are dried fully and weighed accurately. The weight ratio of fully extracted film to the original one is defined as gel content.

The present powdery silicone rubber can be used as toughening agent, processing aids etc., as well as the additives for cosmetics, ink, paints and coatings. The basic usage method is to mix the fully vulcanized powdery silicone rubber in the form of dry crosslinked powder for crosslinked latex with matrix materials in a certain ratio, and process with conventional equipment, wherein suitable amount of processing aid and compatiblizers can be added if required. The use of the fully vulcanized powdery silicone rubber as the modifier for plastics improves physical properties such as the toughness of plastic matrix, and also improves its processing properties and surface gloss.

The present fully vulcanized powdery silicone rubber in the aggregated form has small and uniform particle size, and is very easy to be dispersed in the plastic matrix. It can be mixed with various plastics, as their compatiblizer, processing lubricant or self-lubricant etc., and can be used as additives for cosmetics, ink, paint and coatings, and therefore has great economical significance. In addition, the fully vulcanized powdery silicone rubber is prepared from organosilicon polymer or copolymer latex through irradiation by a simple and inexpensive process, has well controllable particle size and gel content, and is easy to be produced and put into use.

The present invention will be further illustrated in the following by way of the Examples in conjunction with the Figures, which shall not be understood to limit the scope of the invention as defined in the claims.

BRIEF DESCRIPTION OF THE DRAWINGS

FIG. 1 is a transmission electron micrograph of the silicone rubber particle in silicone oil latex vulcanized by irradiation.

EXAMPLE 1

5 kg of a commercially available dimethyl silicone oil latex having a solid content of 30% by weight (available from Beijing Second Chemical Factory, Designation: QR-01, with a viscosity-average molecular weight of 146,000) is placed into a container, 75 g of trimethylolpropane triacrylate is added dropwise while stirring. The stirring is continued for another 1 hour after the addition is complete. Once mixed uniformly, the latex is irradiated by cobalt source, with the irradiation dose being 20 megarads. The irradiated latex is spray-dried with a spray dryer, with the inlet temperature being 130 to 150° C., and the outlet temperature being 40 to 60° C. The dried powdery silicone rubber sample 1 is collected in a cyclone separator. The gel content determined is 81%. The particle size of the latex particle vulcanized by irradiation is about $0.2\mu$ as determined by transmission electron microscopy (see FIG. 1).

EXAMPLE 2

The procedure in Example 1 is repeated except that the irradiation dose used is changed to 15 megarads. A powdery silicone rubber sample 2 is obtained. The gel content determined is 80.5%. The particle size of the latex particle vulcanized by irradiation is about $0.2\mu$ as determined by transmission electron microscopy.

EXAMPLE 3

The procedure in Example 1 is repeated except that the irradiation dose used is changed to 10 megarads. A powdery silicone rubber in sample 3 is obtained. The gel content determined is 79.1%. The particle size of the latex particle vulcanized by irradiation is about $0.2\mu$ as determined by transmission electron microscopy.

EXAMPLE 4

The procedure is Example 1 is repeated except that 30 g of divinylbenzene is used as the crosslinking agent. A powdery silicone rubber sample 4 is obtained. The gel content determined is 79.8%. The particle size of the latex particle vulcanized by irradiation is about $0.2\mu$ as determined by transmission electron microscopy.

EXAMPLE 5

The procedure in Example 1 is repeated except that 60 g of diethylene glycol diacrylate is used as the crosslinking agent and the irradiation dose used is changed to 10 megarads. A powdery silicone rubber sample 5 is obtained. The gel content determined is 80.0%. The particle size of the latex particle vulcanized by irradiation is about $0.2\mu$ as determined by transmission electron microscopy.

EXAMPLE 6

5 kg of a commercially available dimethyl silicone oil latex having a solid content of 30% by weight (available from Shanghai Resin Factory, Designation: 289 type anionic hydroxysilicone oil latex with a viscosity-average molecular weight of 200,000) is placed into a container, 15 g of trimethylolpropane triacrylate is added dropwise while stirring. The stirring is continued for another 1 hour after the addition is complete. Once mixed uniformly, the latex is irradiated by a cobalt source, with the irradiation dose being 15 megarads. The irradiated latex is spray-dried by a spray dryer, with the inlet temperature being 130 to 150° C., and the outlet temperature being 40 to 60° C. The dried powdery silicone rubber sample 6 is collected in a cyclone separator. The gel content determined is 80.8%. The particle size of latex particle vulcanized by irradiation is about $0.15\mu$ as determined by transmission electron microscopy.

EXAMPLE 7

The procedure in Example 6 is repeated except that the irradiation dose used is changed to 10 megarads. A powdery silicone rubber sample 7 is obtained. The gel content determined is 81.1%. The particle size of the latex particle vulcanized by irradiation is about $0.15\mu$ as determined by transmission electron microscopy.

EXAMPLE 8

The procedure in Example 6 is repeated except that the irradiation dose used is changed to 5 megarads. A powdery silicone rubber sample 8 is obtained. The gel content determined is 68.8%. The particle size of the latex particle vulcanized by irradiation is about $0.15\mu$ as determined by transmission electron microscopy.

EXAMPLE 9

The procedure in Example 6 is repeated except that isooctyl acrylate is used as the crosslinking agent. A powdery silicone rubber sample 9 is obtained. The gel content determined is 78%. The particle size of the latex particle vulcanized by irradiation is about $0.15\mu$ as determined by transmission electron microscopy.

EXAMPLE 10

The procedure in Example 6 is repeated except that the crosslinking agent is absent and the irradiation dose used is changed to 7.5 megarads. A powdery silicone rubber sample 10 is obtained. The gel content determined as 73.5%. The particle size of the latex particle vulcanized by irradiation is about $0.15\mu$ as determined by transmission electron microscopy.

What we claim is:

1. A fully vulcanized powdery silicone rubber obtained by vulcanizing silicone oil latex with irradiation, wherein the fully vulcanized powdery silicone rubber has a gel content of at least 60% by weight.

2. The fully vulcanized powdery silicone rubber according to claim 1, comprising fully vulcanized powdery silicone rubber particles having an average particle size of from 0.02 to 1 $\mu$m.

3. The fully vulcanized powdery silicone rubber according to claim 2, wherein the fully vulcanized powdery silicone rubber particles have an average particle size of from 0.05 to 0.5 $\mu$m.

4. The fully vulcanized powdery silicone rubber according to claim 2, wherein the fully vulcanized powdery silicone rubber particles have an average particle size of from 0.05 to 0.1 µm.

5. The fully vulcanized powdery silicone rubber according to claim 1, wherein the fully vulcanized powdery silicone rubber has a gel content of at least 75% by weight.

6. The fully vulcanized powdery silicone rubber according to claim 1, wherein the fully vulcanized powdery silicone rubber comprises fully vulcanized silicone rubber particles having a homogeneous structure.

7. A process for preparing the composition according to claim 1, which comprises vulcanizing a silicone oil latex by means of irradiation in the presence of a crosslinking agent selected from the group consisting of isooctyl (meth) acrylate, glycidyl (meth)acrylate, 1,4-butandiol di(meth) acrylate, 1,6-hexandiol di(meth)acrylate, diethylene glycol di(meth)acrylate, triethylene glycol di(meth)acrylate, neopentyl glycol di(meth)acrylate, divinyl benzene, trimethylolpropane tri(meth)acrylate, pentaerythritol tri(meth) acrylate, pentaerythritol tetra(meth)acrylate, ethoxylated pentaerythritol tetra(meth)acrylate or di-pentaerythritol penta(meth)acrylate, and any combination thereof.

8. The process according to claim 7, comprising irradiating the silicone oil latex with a high-energy source and drying the latex after the irradiation.

9. The process according to claim 8, wherein the high-energy source is selected from the group consisting of cobalt source, X-rays, UV rays and high-energy electron beams.

10. The process according to claim 8, wherein the high-energy source is a cobalt source.

11. The process according to claim 8, wherein the silicone oil latex is irradiated with an irradiation dose in the range of from 5 to 30 megarads.

12. The process according to claim 8, wherein the silicone oil latex is irradiated with an irradiation dose in the range of from 10 to 20 megarads.

13. The process according to claim 7, wherein the crosslinking agent is present in an amount of from 0.1 to 10% by weight, based on a solid content of the silicone oil latex.

14. The process according to claim 7, wherein the crosslinking agent is present in an amount of from 0.5 to 7% by weight based on a solid content of the silicone oil latex.

15. The process according to claim 7, wherein the crosslinking agent is present in an amount of from 0.7 to 5% by weight based on a solid content of the silicone oil latex.

16. The process according to claim 8, wherein the drying is carried out by spray drying with a spray dryer or by precipitation drying.

17. The process according to claim 16, wherein the drying is carried out by spray drying, and an inlet temperature of the spray dryer is controlled at 100 to 200° C., and an outlet temperature of the spray dryer is controlled at 20 to 80° C.

18. A method for processing or toughening a plastic comprising:
   (a) providing the fully vulcanized powdery silicone rubber of claim 1; and
   (b) mixing said fully vulcanized powdery silicone rubber with the plastic.

19. A method for treating a cosmetic, ink, paint or coating comprising:
   (a) providing the fully vulcanized powdery silicone rubber of claim 1, and
   (b) mixing said fully vulcanized powdery silicone rubber with the cosmetic, ink, paint or coating.

20. A fully vulcanized powdery silicone rubber obtained by vulcanizing a silicone oil latex selected from the group consisting of dimethyl silicone oil latex, diethyl silicone oil latex, methylphenyl silicone oil latex, and methyl hydrosilicone oil latex with irradiation in the presence of a crosslinking agent, wherein the fully vulcanized powdery silicone rubber has a gel content of at least 60% by weight.

21. The fully vulcanized powdery silicone rubber according to claim 20, wherein the fully vulcanized powdery silicone rubber has a gel content of at least 75% by weight.

22. The fully vulcanized powdery silicone rubber according to claim 20, wherein the crosslinking agent is present in an amount of from 0.1 to 10% by weight, based on a solid content of the silicone oil latex.

23. The fully vulcanized powdery silicone rubber according to claim 20, wherein the irradiating during the preparation of the fully vulcanized powdery silicone rubber is carried out using a high-energy source in the presence of a crosslinking agent selected from the group consisting of monofunctional, difunctional, trifunctional, tetrafunctional and multifunctional crosslinking agent, and any combination thereof.

24. The fully vulcanized powdery silicone rubber according to claim 23, wherein the crosslinking agent is selected from the group consisting of isooctyl (meth)acrylate, glycidyl (meth)acrylate, 1,4-butandiol di(meth)acrylate, 1,6-hexandiol di(meth)acrylate, diethylene glycol di(meth) acrylate, triethylene glycol di(meth)acrylate, neopentyl glycol di(meth)acrylate, divinyl benzene, trimethylolpropane tri(meth)acrylate, pentaerythritol tri(meth)acrylate, pentaerythritol tetra(meth)acrylate, ethoxylated pentaerythritol tetra(meth)acrylate or di-pentaerythritol penta(meth) acrylate, and any combination thereof.

25. The fully vulcanized powdery silicone rubber according to claim 20, wherein the fully vulcanized powdery silicone rubber comprises fully vulcanized powdery silicone rubber particles having a homogeneous structure.

26. A fully vulcanized powdery silicone rubber obtained by vulcanizing a dimethyl silicone oil latex with irradiation using a high-energy source selected from the group consisting of cobalt source, X-rays, UV rays and high-energy electron beams, in the presence of a crosslinking agent selected from the group consisting of isooctyl (meth) acrylate, glycidyl (meth)acrylate, 1,4-butandiol di(meth) acrylate, 1,6-hexandiol di(meth)acrylate, diethylene glycol di(meth)acrylate, triethylene glycol di(meth)acrylate, neopentyl glycol di(meth)acrylate, divinyl benzene, trimethylolpropane tri(meth)acrylate, pentaerythritol tri(meth) acrylate, pentaerythritol tetra(meth)acrylate, ethoxylated pentaerythritol tetra(meth)acrylate or di-pentaerythritol penta(meth)acrylate, and any combination thereof, the fully vulcanized powdery silicone rubber having a gel content of at least 60% by weight, and the crosslinking agent being present before irradiation in an amount of from 0.1 to 10% by weight, based on a solid content of the silicone oil latex.

27. The fully vulcanized powdery silicone rubber according to claim 26, wherein the fully vulcanized powdery silicone rubber has a gel content of at least 75% by weight.

28. The fully vulcanized powdery silicone rubber according to claim 27, wherein the fully vulcanized powdery silicone rubber comprises fully vulcanized powdery silicone rubber particles having a homogeneous structure.

29. A process for preparing a fully vulcanized powdery silicone rubber, said process consisting essentially of the following steps:
   (a) providing a starting material consisting of silicone oil latex selected from the group consisting of dimethyl silicone oil latex, diethyl silicone oil latex, methylphenyl silicone oil latex, and methyl hydrosilicone oil latex;

(b) vulcanizing the starting material with irradiation in the presence of a crosslinking agent so as to form a fully vulcanized powdery silicone rubber having a gel content of at least 60% by weight, said crosslinking agent being selected from the group consisting of monofunctional, difunctional, trifunctional, tetrafunctional and multifunctional crosslinking agent, and any combination thereof; and (c) drying the latex obtained in step (b).

30. The process according to claim 29, wherein the crosslinking agent is selected from the group consisting of isooctyl (meth)acrylate, glycidyl (meth)acrylate, 1,4-butandiol di(meth)acrylate, 1,6-hexandiol di(meth)acrylate, diethylene glycol di(meth)acrylate, triethylene glycol di(meth)acrylate, neopentyl glycol di(meth)acrylate, divinyl benzene, trimethylolpropane tri(meth)acrylate, pentaerythritol tri(meth)acrylate, pentaerythritol tetra(meth)acrylate, ethoxylated pentaerythritol tetra(meth)acrylate or di-pentaerythritol penta(meth)acrylate, and any combination thereof.

31. The process according to claim 29, the irradiating is carried out using a high-energy source selected from the group consisting of cobalt source, X-rays, UV rays and high-energy electron beams.

32. A process for preparing the fully vulcanized powdery silicone rubber according to claim 1, which comprises vulcanizing a silicone oil latex by means of irradiation in the presence of a crosslinking agent to such an extent that obtained powdery silicone rubber has a gel content of at least 60% by weight.

33. The process according to claim 32, wherein the crosslinking agent is selected from the group consisting of isooctyl (meth)acrylate, glycidyl (meth)acrylate, 1,4-butandiol di(meth)acrylate, 1,6-hexandiol di(meth)acrylate, diethylene glycol di(meth)acrylate, triethylene glycol di(meth)acrylate, neopentyl glycol di(meth)acrylate, divinyl benzene, trimethylolpropane tri(meth)acrylate, pentaerythritol tri(meth)acrylate, pentaerythritol tetra(meth)acrylate, ethoxylated pentaerythritol tetra(meth)acrylate or di-pentaerythritol penta(meth)acrylate, and any combination thereof.

* * * * *